United States Patent [19]

Chandraratna

[11] Patent Number: 5,326,898
[45] Date of Patent: Jul. 5, 1994

[54] SUBSTITUTED PHENYLETHENYL COMPOUNDS HAVING RETINOID-LIKE BIOLOGICAL ACTIVITY

[75] Inventor: Roshantha A. S. Chandraratna, El Toro, Calif.

[73] Assignee: Allergan, Inc., Irvine, Calif.

[21] Appl. No.: 833,688

[22] Filed: Feb. 11, 1992

[51] Int. Cl.$^5$ .......................................... C07C 321/00
[52] U.S. Cl. .......................................... 560/17; 560/9; 560/18; 560/55; 560/65; 562/431; 562/432; 562/474; 564/162; 564/177; 568/325; 568/331; 568/425; 568/439; 568/442; 568/715; 568/807; 568/812; 568/626; 568/659; 568/661; 554/229; 554/231
[58] Field of Search .............. 564/433, 473, 162, 177; 514/543; 560/8, 17, 9, 55, 65, 18; 562/474; 568/425, 439, 442, 715, 807, 812, 626, 659, 661, 325, 331; 554/229, 231

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,801,733 | 1/1989 | Wuest et al. | 560/56 |
| 4,810,804 | 3/1989 | Chandraratna | 514/311 |
| 4,826,969 | 5/1989 | Maignan et al. | 536/55.2 |
| 4,855,320 | 8/1989 | Chatterjee et al. | 514/473 |
| 4,895,868 | 1/1990 | Chandraratna | 514/432 |
| 4,898,833 | 2/1990 | Lang et al. | 514/544 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/543 |
| 5,015,658 | 5/1991 | Chandraratna | 514/432 |
| 5,023,341 | 6/1991 | Chandraratna | 549/23 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |

FOREIGN PATENT DOCUMENTS 0130795 1/1985 European Pat. Off. .... C07D 311/58

OTHER PUBLICATIONS

A General Synthesis of Terminal and Internal Arylalkynes by the Palladium-Catalyzed Reaction of Alkynylzinc Reagents with Aryl Halides by Anthony O. King and Ei-ichi Negishi, *J. Org. Chem* 43 No. 2, 1978 p. 358.

Conversion of Methyl Ketones into Terminal Acetylenes and (E)-Tri-substituted Olefins of Terpenoid Origin by Ei-ichi, Anthony O. King, and William L. Klima, *J. Org. Chem.* 45 No. 12, 1980, p. 2526.

(List continued on next page.)

*Primary Examiner*—José G. Dees
*Assistant Examiner*—Deborah D. Carr
*Attorney, Agent, or Firm*—Gabor L. Szekeres; Robert J. Baran; Martin A. Voet

[57] ABSTRACT

Compounds of the formula

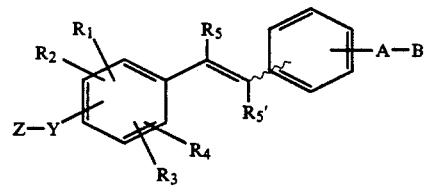

wherein $R_1$, $R_2$, $R_3$ and $R_4$ independently are hydrogen, lower alkyl of 1 to 6 carbons, halogen or lower alkoxy of 1 to 6 carbons; $R_5$ and $R_5'$ independently are hydrogen or lower alkyl of 1 to 6 carbons; Y is oxygen or sulfur; Z is n-alkyl having 2 to 10 carbons, cyclo or branch-chained alkyl of 3 to 10 carbons, and straight chain alkenyl having 2 to 10 carbons, or cyclo or branched chained alkenyl of 3 to 10 carbons, and the Z-Y substituent is in a 1,2 (ortho) or 1,3 (meta) position on the phenyl ring relative to the ethene moiety; A is $(CH_2)_n$ where n is 0-5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds; B is COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2-5 carbons, have retinoid like biological activity.

23 Claims, No Drawings

U.S. PATENT DOCUMENTS

Sporn et al., in *J. Amer. Acad. Derm.* 15:756–764 (1986).
A Convenient Synthesis of Ethynylarenes and Diethynylarenes by S. Takahashi, Y. Kuroyama, K. Sonogashira, N. Hagihara, *Synthesis* 1980 pp. 627–630.
Shudo et al. in *Chem. Phar. Bull.* 33:404–407 (1985).
Kagechika et al. in *J. Med. Chem.* 31:2182–2192 (1988).
Chemistry and Biology of Synthetic Retinoids by Marcia I. Dawson and William H. Okamura, published by CRC Press Inc., 1990, pp. 334–335, 354.
Synthesis of 2,2'-Diacyl-1,1'-biaryls. Regiocontrolled Protection of . . . by Mervic, et al, *J. Org. Chem.*, No. 45, pp. 4720–4725, 1980.

SUBSTITUTED PHENYLETHENYL COMPOUNDS HAVING RETINOID-LIKE BIOLOGICAL ACTIVITY

BACKGROUND OF THE INVENTION

1. Field of the Invention

The present invention is directed to novel compounds which have retinoic acid-like biological activity. More specifically, the present invention relates to 1,2 diphenylalkene (stilbene) derivatives having a 1,3 (meta) or 1,2 (ortho) substituted phenyl ethenyl portion, and a second substituted phenyl portion. The present invention also relates to pharmaceutical compositions comprising these compounds and to methods of using the compounds and compositions.

2. Related Art

U.S. Pat. No. 4,326,055 discloses ethene derivatives which have a substituted phenyl ring and a substituted indane or tetrahydronaphtalene group. The compounds are described as tumor inhibiting agents, and useful for treating dermatological conditions and rheumatic illnesses.

U.S. Pat. No. 4,723,028 discloses certain, (primarily alkyl substituted) 1,2-diphenylethene (stilbene) derivatives which have retinoic acid-like activity.

U.S. Pat. No. 4,740,519 discloses certain aromatic heterocycle derivatives which have retinoic acid like activity.

Published European Patent Application 0 130795 discloses ethene derivatives, where the ethene moiety is substituted by a substituted phenyl group and by a subsitituted chroman, thiochroman or quinoline group. The compounds are useful for inhibiting the degradation of cartilage in mammals.

European Patent Application 176034A (published Apr. 2, 1986) discloses tetrahydronaphtalene compounds having an ethynylbenzoic group. U.S. Pat. No. 4,739,098 discloses compounds wherein three olefinic units from the acid-containing moiety of retinoic acid are replaced by an ethynylphenyl functionality. These compound have retinoic acid-like biological activity.

U.S. Pat. No. 4,810,804 (issued on Mar. 7, 1989) based on an application of the same inventor and assigned to the same assignee as the present application, discloses such disubstituted acetylene compounds wherein one of the substituents of the acetylene (ethyne) group is a substituted phenyl group, and the second substituent is a substituted or unsubstituted 6-chromanyl, 6-thiochromanyl or 6-tetrahydroquinolinyl group. The compounds disclosed and claimed in U.S. Pat. No. 4,810,804 have retinoic acid-like biological activity.

Several co-pending applications and recently issued patents of the present inventor, which are assigned to the assignee of the present application, are directed to further compounds having retinoic acid-like activity.

A published European patent application of the present applicant (Publication No. 0284288, published on Sep. 28, 1988) describes compounds having retinoic acid-like activity which are 4,4 disubstituted chroman-6-yl, 4,4 disubstituted thiochroman-6-yl acetylenes also substituted by a substituted heteroaryl group.

An article in the Journal of Organic Chemistry 1980 45, 4720–4725, discloses certain methoxy substituted diphenyl ethane (stilbene) derivatives as synthetic intermediates in the synthesis of certain phenanthrene derivatives.

Retinoic acid-like activity has been generally recognized in the art to be associated with useful biological activity. Specifically, compounds having retinoic acid-like activity are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointiural hyperproliferation, for treating and preventing other non-malignant hyperproliferative diseases such as endometrial hyperplasia, benign prostatic hypertrophy, proliferative vitreal retirropalhy and dysplasias, for treating autoimmune diseases and immunological disorders (e.g. lupus erythematosus, for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

SUMMARY OF THE INVENTION

This invention covers compounds of Formula 1

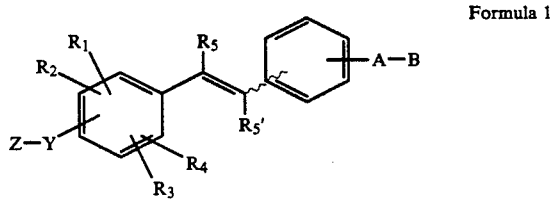

Formula 1 wherein
$R_1$, $R_2$, $R_3$ $R_4$ independently are hydrogen, lower alkyl of 1 to 6 carbons, halogen or lower alkoxy of 1 to 6 carbons;

$R_5$ and $R_5'$ independently are hydrogen, lower alkyl of 1 to 6 carbons or halogen;

Y is oxygen or sulfur;

Z is n-alkyl having 2 to 10 carbons, cyclo or branch-chained alkyl of 3 to 10 carbons, and straight chain alkenyl having 2 to 10 carbons, or cyclo or branched chained alkenyl of 3 to 10 carbons, and the Z-Y substituent is in a 1,2 (ortho) or 1,3 (meta) position on the phenyl ring relative to the ethene moiety;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is COOH or a pharmaceutically acceptable salt thereof, $COOR_8$, $CONR_9R_{10}$, $—CH_2OH$, $CH_2OR_{11}$, $CH_2OCOR_{11}$, CHO, CH $(OR_{12})_2$, $CHOR_{13}O$, $—COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2-5 carbons.

In a second aspect, this invention relates to the use of the compounds of Formula 1 as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myelorid leukemias, for reversing and preventing atherosclerosis and restenosis resulting from neointiural hyperproliferation, for treating and preventing other non-malignant hyperproliferative diseases such as endometrial hyperplasia, benign prostatic hypertrophy, proliferative vitreal retirropalhy and dysplasias, for treating autoimmune diseases and immunological disorders (e.g. lupus erythematosus, for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with a compound of Formula 3

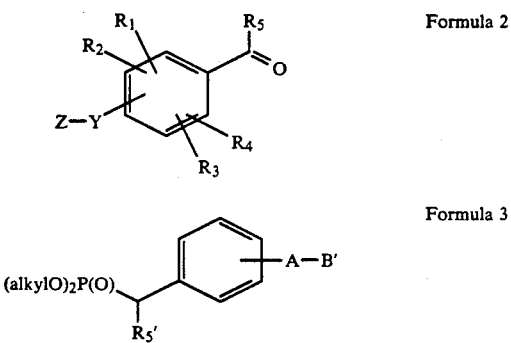

Formula 2

Formula 3 in which $R_1$ through $R_5$, $R'_5$, A, Y and Z are defined as in connection with Formula 1, and the Z-Y group is in a 1,2 (Ortho) or in 1,3 (meta) position relative to the $R_5$-CO group, and B' is defined as B in Formula 1 above, or as such a precursor of B which can be readily converted into B by a chemical reaction or reactions well known in the art and within the skill of the practicing organic chemist. The reaction between compounds of Formula 2 and of Formula 3 is conducted under conditions typical for the Horner-Emmons modification of the Wittig reaction hereinafter referred to as "Wittig-type" or "modified Wittig" reactions), and the present invention also relates to reactions between the compounds of these formulas and of analogous formulas under Wittig-type or modified Wittig conditions to provide the compounds of Formula 1. Furthermore, the present invention also relates to reactions performed on compounds of Formula 1 (or on its precursors) to obtain still further compounds of Formula 1, such reactions including:

homologating a compound of the Formula 1 where A is $(CH_2)_n$ and n is 0–4 to give an acid of Formula 1; or converting an acid of Formula 1 to a salt; or forming an acid addition salt;
converting an acid of Formula 1 to an ester; or
converting an acid of Formula 1 to an amide; or
reducing an acid of Formula 1 to an alcohol or aldehyde; or
converting an alcohol of Formula 1 to an ether or ester; or
oxidizing an alcohol of Formula 1 to an aldehyde; or
converting an aldehyde of Formula 1 to an acetal; or
converting a ketone of Formula 1 to a ketal.

GENERAL EMBODIMENTS Definitions

The term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. Where B (of Formula.1) is —COOH, this term covers the products derived from treatment of this function with alcohols, preferably with aliphatic alcohols having 1-6 carbons. Where the ester is derived from compounds where B is —CH$_2$OH, this term covers compounds of the formula —CH$_2$OOCR$_{11}$ where R$_{11}$ is any substituted or unsubstituted aliphatic, aromatic or aliphatic-aromatic group, preferably with 1-6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2–5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention contain at least one double bond and therefore may have trans and cis (E and Z) isomers. In addition, some of the compounds of the present invention may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference to the symbols $R_1$ through $R_4$ in Formula 1, in the preferred compounds of the present invention these symbols preferably represent hydrogen or lower alkyl groups. Particularly preferred are those compounds where $R_1$ through $R_4$ are all hydrogen and those where the three out of the four of the above-mentioned groups is hydrogen, and one is lower alkyl. Still further preferred among these are compounds where the lower alkyl group is methyl.

With regard to the groups $R_5$ and $R'_5$ in the compounds of Formula 1, compounds are preferred where $R_5$ and $R'_5$ are independently from one another, hydrogen or methyl.

The symbol Y represents either oxygen or sulfur in accordance with the present invention, with preference for Y being sulfur.

With regard to the symbol Z in Formula 1, compounds of the invention are preferred where Z represents a branched chain alkyl or branched chain alkenyl group having one double bond. Particularly preferred are compounds where Z represents 3-methyl-2-butenyl.

With regard to the substitution pattern on that phenyl moiety of the compounds of the present invention which bears the Z-Y group, compounds are preferred where the Z-Y and ethenyl groups respectively occupy the 1 and 3 or 1 and 2 positions on the phenyl ring (the substitution is meta or ortho), and where the $R_1$ through $R_4$ groups are hydrogen. Alternatively, compounds are preferred where the Z-Y and ethenyl groups occupy the 1 and 3 or 1 and 2 (meta or ortho) positions, $R_1$ through $R_3$ are hydrogen, and $R_4$ is methyl and occupies the 6 position (ortho' to the ethenyl group). The most preferred are those compounds where the Z-Y group and the ethene moiety are 1,3 (meta) to one another.

With regard to the substitution pattern on the other phenyl moiety of the molecule (which bears the A-B group) compounds are preferred where the A-B group and the ethene moiety are 1,4 (para) to one another.

With regard to the side chain (substituent A) on the phenyl group, compounds are preferred where A is $(CH_2)_n$, and still more preferred where n is 0.

With respect to the symbol B, the compounds of the invention are preferred where B is —COOH, or an alkali metal salt or organic amine salt thereof. Alternatively, compounds are preferred where B is represented by $COOR_8$ (ester where $R_8$ is lower alkyl), $CONR_9R_{10}$ (amide) —$CH_2OH$ (alcohol), $CH_2OCOR_{11}$, $CH_2OR_{11}$ ($R_{11}$ is lower alkyl; lower alkyl esters and ethers formed with a lower alkanol) or B is —CHO or $CH(OR_{12})_2$, $CHOR_{13}O$ (acetal derivatives), where $R_{12}$ and $R_{13}$ are defined as in connection with Formula 1. The most preferred compounds of the invention are shown in Formula 4:

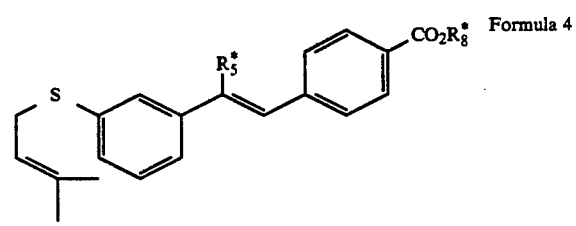

| | |
|---|---|
| Compound 1 | $R_5^* =$ H and $R_8^* =$ ethyl; |
| Compound 2 | $R_5^* =$ H and $R_8^* =$ H; |
| Compound 3 | $R_5^* =$ methyl and $R_8^* =$ ethyl; |
| Compound 4 | $R_5^* =$ methyl and $R_8^* =$ H; |

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retionic-acid like activity of these compounds was confirmed through the classic measure of retionic acid activity involving the effects of retionic acid on ornithine decarboxylase. The original work on the correlation between retinoic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoyl-phorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*, 35: 1662–1670, 1975.

By way of example of retinoic acid-like activity it is noted that in the assay conducted essentially in accordance with the method of Verma & Boutwell, ibid, the following examples of the preferred compounds of the present invention (Compounds 1, 2 and 3) attained an 80% inhibition of TPA induced ODC activity at the following concentrations ($IC_{80}$):

| Compound | $IC_{80}$ conc (nmols) |
|---|---|
| 1 | 209 |
| 2 | 512 |
| 3 | 91 |

SPECIFIC EMBODIMENTS

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Generally speaking the compounds of the present invention can be prepared by Horner-Emmons, Wittig or analogous (modified Wittig) reaction between the compounds of Formula 2 and Formula 3, as described above. In this reaction, shown in Reaction Scheme 1, the appropriately substituted phenyl aldehyde or ketone of Formula 2 reacts with the dialkyl (preferably diethyl) phosphonate of Formula 3 derived from the desired phenyl compound, to form an ethene linkage between the phenyl moiety substituted with Z-Y- and the second phenyl moiety substituted with the A-B- group in accordance with the invention. Generally speaking, the Wittig reaction is conducted in the presence of a strong base, such as sodium hydride (NaH) or dimsyl sodium ($NaCH_2SOCH_3$) in a polar solvent such as dimethylsulfoxide. The coupling of the reagents of Formula 2 and Formula 3 provides the compounds of Formula 1 or of Formula 5.

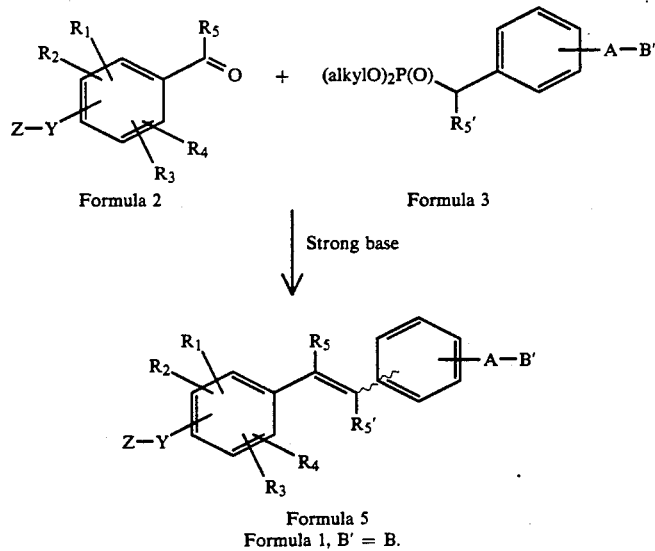

REACTION SCHEME 1

The compounds of Formula 5 differ from the compounds of Formula 1 only in that the symbol B' represents such a group which may be readily converted by reactions well known in the art to a group represented by the symbol B. Compounds of Formula 1 may also be converted to still other compounds represented by Formula 1 with reactions which are known in the art. The A-B and or A-B' functionality of the compounds of Formula 3 can be prepared by well known and published methods of synthetic organic chemistry. By way of example, carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before effecting the Wittig (or analogous) coupling reaction of Reaction Scheme 1 (where such compounds are not available from a commercial source) the derivatives of Formula 3 where B is —COOH are subjected to homologation by successive treatment under Arndt-Eistert conditions or other homologation procedures. Alternatively, derivatives where B is different from COOH, may also be homologated by appropriate procedures. The homologated acids can then be esterified by the general procedure outlined in the preceding paragraph.

An alternative means for making compounds where A is $(CH_2)_n$ (n is 1-5) is to subject the compounds of Formula 1, where B is an acid or other function, to homologation, using the Arndt-Eistert method referred to above, or other homologation procedures.

Compounds of Formula 1 where A is an alkenyl group having one or more double bonds can be made for example, by having the requisite number of double bonds incorporated into the intermediate of Formula 3.

Generally speaking, the compounds of Formula 3 where A is an unsaturated carbon chain can be obtained by synthetic schemes well known to the practicing organic chemist; for example by Wittig and like reactions, or by introduction of a double bond by elimination of halogen from an alpha-halo-heteroarylalkyl-carboxylic acid, ester or like carboxaldehyde. Compounds of Formula 1 where the A group has a triple (acetylenic) bond can be made by using the corresponding intermediate of Formula 3. Such intermediate can be obtained by reactions well known in the art, for example, by reaction of a corresponding phenyl-methyl ketone with strong base, such as lithium diisopropyl amide.

The acids and salts derived from Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about $-10$ degrees and $+10$ degrees C. The last mentioned solution is then stirred at the reduced temperature for 1-4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1-4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K. Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where B is H can be prepared from the corresponding halogenated phenyl compounds, preferably where the halogen is I.

The intermediate compounds of general Formula 2 are prepared in accordance with the generalized reaction steps outlined in Reaction Scheme 2.

REACTION SCHEME 2

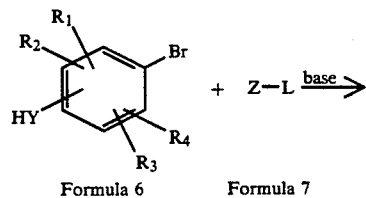

Formula 6   Formula 7

-continued
REACTION SCHEME 2

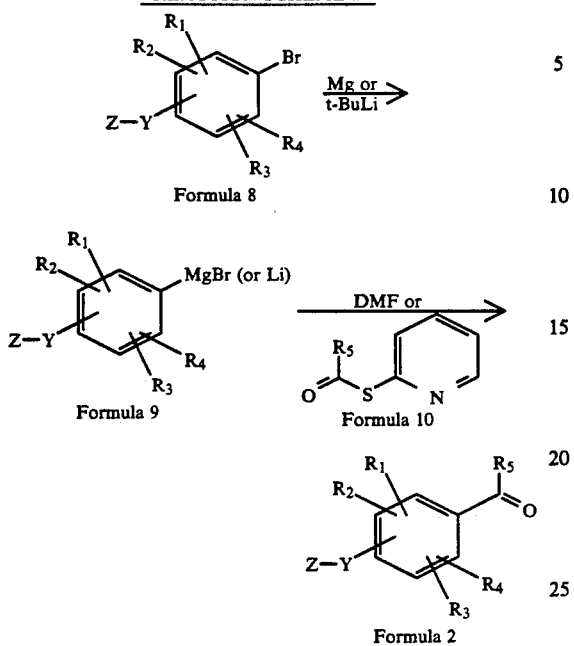

Formula 8

Formula 9

Formula 10

Formula 2

In accordance with this scheme, the starting material is a halogenated phenol or thiophenol of Formula 6 where the halogen and SH or OH groups are in 1,3 (meta) or in 1,2 (ortho) positions relative to one another and which also has the desired $R_1$ through $R_4$ substituents. The general formula indicates a bromo phenol or thiophenol, however instead of bromine another halogen may be used. Examples for the starting material of Formula 6 which are either available commercially, or can be prepared in accordance with reactions well known in the art, are 3-bromothiophenol, 6-methyl-3-bromothiophenol, 3-bromophenol, 6-methyl-3-bromophenol, 2-bromothiophenol, 6-methyl-2-bromothiophenol, 2-bromophenol, 6-methyl-2-bromophenol.

The compound of Formula 6 is reacted under basic conditions with a compound of the formula Z-L (Formula 7) where Z is defined as in connection with Formula 1, and L symbolizes a leaving group, such as halogen, mesyl, tosyl or the like. Generally speaking, the reaction between the compounds of Formula 6 and Formula 7 is performed under alkylating conditions. The ether or thioether obtained in the foregoing reaction, which is shown by Formula 8, is thereafter converted to a Grignard or like reagent, shown by Formula 9. Specifically, Formula 9 shows a Grignard reagent derived from a bromophenyl alkyl ether or from the bromophenyl alkyl thioether of Formula 8, which is obtained under conditions known in the art for forming Grignard reagents of this type. Alternatively, Formula 9 shows a lithium reagent derived from the bromophenyl alkyl ether or from the bromophenyl alkyl thioether of Formula 8 under conditions of a metal halogen exchange reaction, such as treatment with n-butyl lithium. The Grignard or lithium reagent of Formula 9 is thereafter reacted with dimethylformamide to provide the substituted benzaldehyde (Formula 2 where $R_5$ is H), or with a reagent comprising a source for the $R_5$—CO— group such as the acyl-thiopyridine of Formula 10 An alternative source for the $R_5$—CO group where $R_5$ is methyl, is the reagent N,O-dimethylhydroxylacetamide.

The intermediate compounds of general Formula 3 are prepared in accordance with the generalized reaction steps outlined in Reaction Scheme 3.

REACTION SCHEME 3

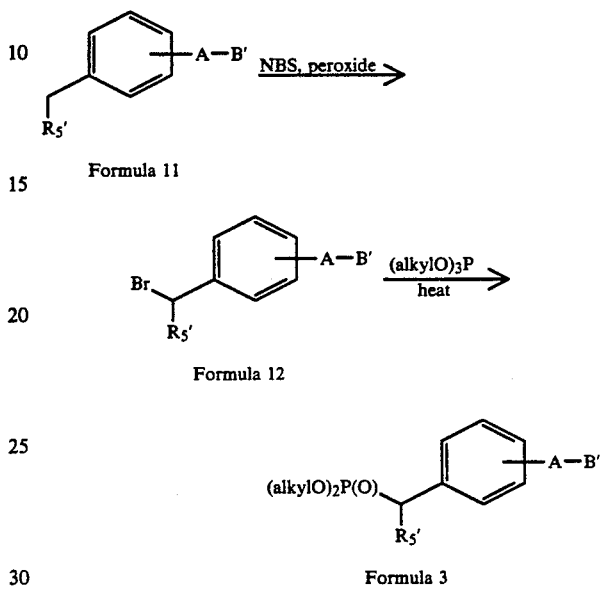

Formula 11

Formula 12

Formula 3

In accordance with Reaction Scheme 3, and in general terms, the alkylphenyl derivative of Formula 11 serves as a starting material. This compound bears either the A-B substituent (as the symbols A and B are defined in connection with Formula 2, or the A-B' substituent, wherein B' is defined as in connection with Formula 3. The compound of Formula 11 also bears an alkyl group in the position where the ethene moiety of the compounds of the invention (Formula 2) is attached. In the event $R_5'$ is hydrogen then this alkyl group is simply methyl. The starting materials of Formula 11 are either commercially available or can be obtained in accordance with synthetic procedures known in the art. In the event the starting compound has a carboxylic acid function, it is esterified by a procedure established in the art (such as reaction with ethyl alcohol in the presence of dicyclohexylcarbodiimide (DCC)) and the resulting ester (or other intermediate corresponding to Formula 11) is reacted with N-bromosuccinimide and benzoyl peroxide to provide the bromo compound of Formula 12. The compound of Formula 12 is thereafter reacted with a trialkylphosphite (preferably triethylphosphite) to provide the phosphonate of Formula 3. For the synthesis of the preferred compounds of the present invention which are derivatives of p-toluic acid (in Formula 1 A is $(CH_2)_n$, n is zero, and the ethene moiety is 1,4 (para) to the carboxylic acid or ester function) the synthesis corresponding to the intermediate of Formula 3 may start with commercially available (Aldrich) α-bromo-p-toluic acid (4-carboxybenzylbromide). This compound is esterified with ethyl alcohol to provide a suitable intermediate corresponding to Formula 12, which is thereafter reacted with triethylphosphite to provide the intermediate corresponding to Formula 3.

An alternate synthetic route for making compounds of Formula 1 is the reaction between the phosphonium salt of Formula 13 and the aldehyde or ketone of Formula 14, as is indicated in Reaction Scheme 4. Still another synthetic route leading to the compounds of Formula 1 is the reaction between the aldehyde or ketone of Formula 15 and the phosphonium salt of Formula 16, as indicated in Reaction Scheme 5. In these formulas and reaction schemes the symbols $R_1-R_5$, $R_5'$, Z-Y, and A and B' are defined as above.

Several other synthetic routes and methods for the preparation of the compounds of the present invention may become readily apparent to those skilled in the art in light of the present disclosure.

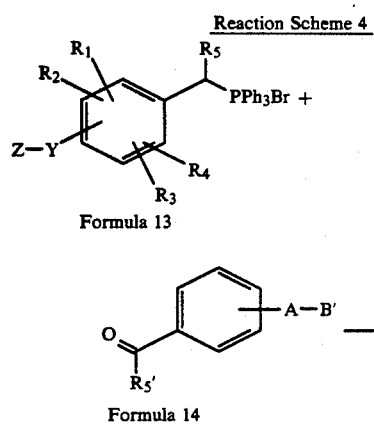

Formula 13

Formula 14

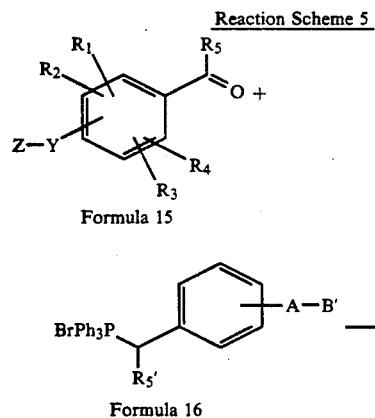

Formula 15

Formula 16

SPECIFIC EXAMPLES
3-(3-Methyl-2-thiobuten-l-yl)bromobenzene (Compound 10)

A mixture of 5.0 g (24.6 mmol) of 3-bromothiophenol and 1.08 g (27.1 mmol) sodium hydroxide in 25 mL acetone was heated to reflux under argon for 2.5 hours. The refluxing mixture was then treated dropwise with a solution of 3.12 mL (27.1 mmol) of 4-bromo-2-methyl-2-butene in 5 mL acetone and the mixture heated to reflux for an additional 24 hours. The mixture was then cooled to room temperature and the solvent removed in-vacuo. The residue was treated with 25 mL of water and extracted with 3×40 mL ether.

The ether extracts were combined and washed successively with 3×15 mL of 5% NaOH, 25 mL of water and 25 mL saturated aqueous NaCl and then dried (MgSO4). The solvent was removed in-vacuo and the residual oil purified by Kugelrohr distillation (125° C., 15 mm Hg) to give the title compound as a clear, colorless oil.

PMR (CDCl3): δ 1.62 (3H, s), 1.73 (3H, s), 3.54 (2H, d, J=7.8 Hz), 5.28 (1H, t, J=7.8 Hz), 7.12 (1H, dd, J=7.1, 7.1 Hz), 7.23 (1H, ddd, J=0.7, 1.7, 7.1 Hz), 7.29 (1H, dd, J=0.7, 1.7, 7.1 Hz), 7.44 (1H, dd, J=0.7, 1.7 Hz).

3-(3-methyl-2-thiobuten-l-yl)benzaldehyde (Compound 11)

To a −78° C. solution of 1.5 g (5.83 mmol) of 3-(3-methyl-2-thiobuten-l-yl ) bromobenzene (Compound 10 ) and 25 mL THF under argon was added dropwise 2.56 mL of a 2.5 M solution of n-butyllithium and hexane (5.83 mmol). After 15 minutes, 7.0 mL (87.8 mmol) of N,N-dimethylformamide was added dropwise and the solution was allowed to warm to 0° C. in an icewater bath and stirred for an additional hour. The solution was treated with 15 mL of water and extracted with 3×75 mL ether.

The ether extracts were combined and washed with 75 mL saturated aqueous NaCl and then dried (MgSO4). The solvent was removed in-vacuo and the residual oil purified by flash chromatography (SiO2, 95:5, hexane:ethyl acetate) to give the title compound as a clear, colorless oil.

PMR (CDCl3): δ 1.63 (3H, s), 1.73 (3H, s), 3.60 (2H, d, J=7.7 Hz), 5.30 (1H, t, J=7.7 Hz), 7.43 (1H, dd, J=7.6, 7.6 Hz), 7.56 (1H, dd, J=2.0, 3.3 Hz), 7.65 (1H, dd, J=1.5, 7.6 Hz), 7.80 (1H, d, J=1.5 Hz), 9.97 (1H, s).

2-Pyridylthioacetate (Compound 12)

A solution of 12.5 mL (90 mmol) of triethylamine, dimethylaminopyridine and 13 mL dichloromethane was added dropwise to a solution of 5 g (44.5 mmol) of 2-pyridinethiol and dichloromethane (130 mL) at 0° C. under argon. After 5 minutes, 4.16 mL (58.5 mmol) of acetyl chloride was added dropwise and the solution was stirred at 0° C. for 30 minuted and then at room temperature for 3 hours. The solution was treated with 10 mL of 10% aqueous HCl and the layers separated.

The organic layer was washed with 100 mL water, 100 mL saturated aqueous NaHCO3, 100 mL saturated aqueous NaCl and then dried (MgSO4). The solvent was removed in-vacuo and the residual oil purified by bulb-to bulb distillation (bp −90° C. 2 mm Hg)) to give the title compound as a clear, yellow oil.

PMR (CDCl3): δ 2.50 (3H, s), 7.30 (1H, dd, J=4.9, 7.4 Hz), 7.62 (1H, d, J=8.5 Hz), 7.75 (1H, dd, J=5.9, 7.8 Hz), 8.62 (1H, dd, J=2.0, 4.9 Hz).

3-(3-methyl-2-thiobuten-l-yl)acetophenone (Compound 13)

To a −78° C. solution of 1.5 g (5.83 mmol) of 3-(3 -methyl-2-thiobuten-l-yl)bromobenzene (Compound 12) and 25 mL THF under argon was added dropwise 2.56 mL of a 2.5 M solution 5.83 mmol) of n-butyllithium and hexane. After 15 minutes, 0.57 g (5.52 mmol) of N,O-dimethylhydroxylacetamide was added dropwise and the solution was allowed to warm to 0° C. in an ice-water bath and stirred for an additional hour. The solution was treated with 15 mL of dilute HCl and extracted with 3×75 mL ether.

The ether extracts were combined and washed with 75 mL saturated aqueous NaCl and then dried (MgSO4). The solvent was removed in-vacuo and the residual oil purified by flash chromatography (SiO2, 95:5, hexane:ethyl acetate) to give the title compound as a clear, pale yellow oil.

PMR (CDCl3): δ 1.61 (3H, s), 1.72 (3H, S), 2.59 (3H, s), 3.58 (2H, d, J=7.7 Hz), 5.30 (1H, t, J=7.7 Hz), 7.36

(1H, dd, J=7.7, 7.7 Hz), 7.50 (1H, d, J=7.7 Hz), 7.74 (1H, d, J=7.7 Hz), 7.89 (1H, s).

4-Carboethoxybenzyl bromide (Compound 14)

To a stirred solution of 16.09 g (78 mmol) of 1,3-dicyclohexylcarbodiimide (Aldrich) in 100 ml methylene chloride was added a suspension of 15.4 g (71 mmol) of 4-carboxybenzyl bromide in 100 ml methylene chloride and then 4.9 g (106.5 mmol) of absolute ethanol and 0.81 g (7.1 mmol) of 4-dimethylaminopyridine. A further 50 ml of methylene chloride was added to the reaction mixture and mixture heated at reflux for 2 hours. The mixture was allowed to cool to room temperature and the resultant white precipitate removed by filtration. The filtrate was washed with water, dried (MgSO4) and then concentrated in-vacuo to give the title compound as a colorless oil which crystallized on standing. PMR (CDCl3); δ 1.39 (3H, t, J=7.2 Hz), 4.38 (2H, q, J=7.2 Hz), 4.50 (2H, s), 7.45 (2H, d, J=7.7 Hz), 8.03 (2H, d, J=7.7 Hz).

Diethyl (4-carboethoxybenzyl) phosphonate (Compound 15)

A mixture of 11.8 g (48 mmo 1) o f 4-carboethoxybenzyl bromide (Compound 14) and 12.0 g (72 mmol) of freshly distilled triethylphosphite was placed in a flask fitted with an argon inlet and a dry-ice cooled trap. A continuous stream of argon was passed over the stirred reaction mixture and mixture heated at 120° C. for 3 hours at which time no further ethyl bromide was being formed. The residue was purified by vacuum distillation to give the title compound as a colorless oil, BP=170°/0.35 mm). PMR (CDCl3): δ 1.23 (6H, t, J=7.1 Hz), 1.39 (3H, t, J=6.9 Hz), 3.21 (2H, d, J=22.1 Hz), 4.02 (4H, m), 4.37 (2H, q, J=7.5 Hz), 7.38 (2H, d, J=7.9 Hz), 8.00 (2H, d, J=7.9 Hz).

Ethyl 4-(E-2-(3-(3-methyl-2-thiobuten-1-yl)phenyl)ethenyl) benzoate (Compound 1)

400 mg 0f 60% NaH in mineral oil was washed successively with three 5-mL portions of hexane. The residual hexane was removed under vacuum and the vacuum was broken with dry argon. 10 ml of dimethy sulfoxide (DMSO) was added and the resulting suspension was heated to 60° C. for 1 hour to produce a 1 M solution of dimsyl sodium. 2.00 mL of dimsyl sodium was added to 0.661 g (2.20 mmol) of diethyl (4carboethoxybenzyl)phosphonate (Compound 15) and the resulting rust-colored solution was stirred for 30 minutes at room temperature under argon. This solution was added to 0.206 g (1.0 mmol) of 3-(3-methyl-2-thiobutenyl) benzaldehyde (Compound 11) and 3.5 mL DMSO and this solution was stirred for an additional 1.0 hours. The mixture was treated with 10 mL of water and extracted with 3×25 mL ethyl acetate.

The ethyl acetate extracts were combined and washed with 25 mL saturated aqueous NaCl and then dried 5 (MgSO4). The solvent was removed in-vacuo and the residual oil purified by flash chromatography (SiO2, 95:5, hexane:ethyl acetate) to give the title compound as a light yellow solid.

PMR (CDCl3): δ1.40 (3H, t, J=7.2 Hz), 1.61 (3H, s), 1.73 (3H, s), 3.57 (2H, d, J=7.7 Hz), 4.38 (2H, q, J=7.2 Hz), 5.33 (1H, t, J=7.7 Hz), 7.09 (1H, d, J=16.4 Hz), 7.16 (1H, d, J=16.4 Hz), 7.30 (3H, m), 7.49 (1H, s), 7.55 (2H, d, J=8.4 Hz), 8.03 (2H, d, J=8.4 Hz).

Ethyl 4-(E-2-(3(3-methyl-2-thiobuten-1-yl) phenyl) propen-1-yl) benzoate (Compound S)

400 mg of 60% NaH in mineral oil was washed successively with three 5-mL portions of hexane. The residual hexane was removed under vacuum and the vacuum was broken with dry argon. 10 ml of dimethyl sulfoxide (DMSO) was added and the resulting suspension was heated to 60° C. for 1 hour to produce a 1 M solution of dimsyl sodium. 2.00 mL of dimsyl sodium was added to 0.66 g (2.2 mmol) of diethyl (4-carboethoxybenzyl) phosphonate (Compound 15) and the resulting rust-colored solution was stirred for 30 minutes at room temperature under argon. This solution was added to 0.22 g (1.00 mmol) of 3-(3-methyl-2-thiobuten-1-yl)acetophenone (Compound 13) and 3.5 mL DMSO and this solution was stirred for an additional 2.0 hours. The solution was treated with 0.60 mL of a 2.0 M solution of NaOEt and EtOH and the solution stirred an additional 12 hours at room temperature. The mixture was poured into 10 mL of 1% aq. HCl and extracted with 3×50 mL ethyl acetate.

The ethyl acetate extracts were combined and washed with 25 mL saturated aqueous NaCl and then dried (MgSO4). The solvent was removed in-vacuo and the residual oil purified by flash chromatography (SiO2, 98:2, hexane:ethyl acetate) and recrystalization (EtOH) to give the title compound as a light yellow crystaline solid.

PMR (CDCl3): δ 1.41 (3H, t, J=7.1 Hz), 1.61 (3H, s), 1.73 (3H, s), 2.28 (3H, s), 3.57 (2H, d, J=7.7 Hz), 4.39 (2H, q, J=7.1 Hz), 5.31 (1H, t, J=7.7 Hz), 6.82 (1H, s), 7.27–7.35 (3H, m), 7.41 (2H, d, J=8.3 Hz), 7.48 (1H, s), 8.05 (2H, d, J=8.3 Hz).

4- (E-2-(3-(3-methyl-2-thiobuten-1-yl) phenyl)ethenyl)benzoic acid (Compound 2)

To a solution of 225 mg of ethyl 4- (E-2-(3-(3-methyl-2-thiobuten-1-yl)phenyl)ethenyl)benzoate (Compound 1) in 10 mL of ethanol under argon was added dropwise 2 mL of a 2N solution of aqueous potassium hydroxide. The solution was stirred at room temperature for 18 hours, cooled in an ice-water bath and acidified with 3N aqueous hydrochloric acid. The resulting precipitate was extracted into ether, the layers separated and the ether layer washed with saturated aqueous sodium chloride, dried (MgSO4), and concentrated under reduced pressure. The resulting solid was recrystalized from ethanol to give the title compound.

PMR (CDCl3): δ 1.62 (3H, s), 1.74 (3H, s), 3.59 (2H, d, J=7.7 Hz), 5.33 (1H, t, J=7.7 Hz), 7.13 (1H, d, J=16.2 Hz), 7.26–7.36 (3H, m), 7.51 (1H, s), 7.60 (2H, d, J=8.3 Hz), 8.11 (2H, d, J=8.2 Hz).

4-(E-2-(3-(3-Methyl-2-thiobuten-1-yl)phenyl)propen-1-yl)benzoic acid (Compound 4)

To a solution of 105 mg of ethyl 4-(E-2-(3-(3-methyl-2-thiobuten-1-yl)phenyl)propen-1-yl)benzoate (Compound 3) in 3 mL of ethanol under argon was added dropwise 1 mL of a 2N solution of aqueous potassium hydroxide. The solution was stirred at room temperature for 18 hours, cooled in an ice-water bath and acidified with 3N aqueous hydrochloric acid. The resulting precipitate was extracted into ether, the layers separated and the ether layer washed with saturated aqueous sodium chloride, dried (MgSO4), and concentrated under reduced pressure. The resulting solid was recrystalized from toluene/hexane to give the title compound.

PMR (CDCl$_3$): δ 1.61 (3H, s), 1.73 (3H, s), 2.30 (3H, s), 3.59 (2H, d, J=7.7 Hz), 5.32 (1H, t, J=7.7 Hz), 6.84 (1H, s), 7.25–7.35 (2H, m), 7.45 (2H, d, J=8.3 Hz), 7.49 (1H, s), 8.13 (2H, d, J=8.3 Hz).

The following further examplary compounds of the invention can be prepared in an analogous manner by the Wittig reaction (coupling) of the following intermediates:

E and Z ethyl 3-(2-(3-(3-methyl-2-thiobuten-1-yl)phenyl-ethenyl benzoate from 3-(3-methyl-2-thiobute-1-yl)-benzaldehyde and diethyl (3-carboethoxybenzyl)-phosphonate;

E and Z ethyl 2-(2-(3-(3-methyl-2-thiobuten-1-yl)phenyl-ethenyl benzoate from 3-(3-methyl-2-thiobute-1-yl)-benzaldehyde and diethyl (2-carboethoxybenzyl)-phosphonate;

E and Z ethyl 4-(2-(3-(3-methyl-2-thiobuten-1-yl)2-methyl)phenyl)ethenyl) benzoate from 3-(3-methyl-2-thiobutenyl)-2-methylbenzaldehyde and diethyl (4-carboethoxybenzyl)phosphonate;

E and Z ethyl 3-(2-(3-(3-methyl-2-thiobuten-1-yl)phenyl)propen-1-yl) benzoate from 3-(3-methyl-2-thiobuten-1-yl)acetophenone and diethyl (3-carboethoxybenzyl)phosphonate, and 3-(2-(3-(3-methyl-2-thiobuten-1-yl)-2-methyl)phenyl)-propen-1-yl) benzoate from 3-(3-methyl-2-thiobutenyl)-2-methyl)acetophenone and diethyl (3-carboethoxybenzyl)phosphonate.

What is claimed is:

1. A compound of the formula

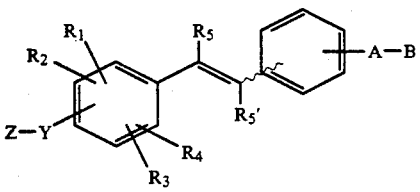

wherein
R$_1$, R$_2$, R$_3$ and R$_4$ independently are hydrogen, lower alkyl of 1 to 6 carbons, halogen or lower alkoxy of 1 to 6 carbons;
R$_5$ and R$_5'$ independently are hydrogen, lower alkyl of 1 to 6 carbons or halogen;
Y is oxygen or sulfur;
Z is branch-chained alkyl of 3 to 10 carbons, and straight chain alkenyl having 2 to 10 carbons, or cyclo or branched chained alkenyl of 3 to 10 carbons, and the Z-Y substituent is in a 1,2 (ortho) or 1,3 (meta) position on the phenyl ring relative to the ethene moiety;
A is (Ch$_2$)$_n$ where n is 0–5, lower branched chain alkyl having 3 to 6 carbons, cycloalkyl having 3 to 6 carbons, alkenyl having 2 to 6 and 1 or 2 double bonds, alkynyl having 2 to 6 carbons and 1 or 2 triple bonds;
B is COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5 to 10 carbons, or phenyl or lower alkylphenyl, R$_{11}$ is alkyl of 1 to 10 carbons, phenyl or lower alkylphenyl, R$_{12}$ is lower alkyl, and R$_{13}$ is divalent alkyl radical of 2–5 carbons.

2. A compound of claim 1 wherein R$_1$ through R$_4$ are hydrogen.

3. A compound of claim 1 wherein one of R$_1$ through R$_4$ is lower alkyl and the others are hydrogen.

4. A compound of claim 3 wherein the lower alkyl group is in the 2-position of the phenyl ring.

5. A compound of claim 1 wherein Z is a branched chain alkenyl group.

6. A compound of claim 1 wherein the Z-Y-substituent is in the 3 position of the phenyl group.

7. A compound of claim 1 wherein the Z-Y-substituent is in the 2 position of the phenyl group.

8. A compound of claim 1 wherein B is COOH or a pharmaceutically acceptable salt thereof, or where B is COOR$_8$, or CONR$_9$R$_{10}$.

9. A compound of claim 8 where A is (CH$_2$)$_n$ and n is 0 to 3.

10. A compound of the formula

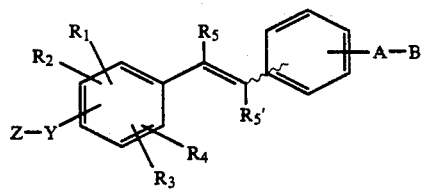

where
R$_1$, R$_2$, R$_3$ and R$_4$ independently are hydrogen, lower alkyl of 1 to 6 carbons, halogen or lower alkoxy of 1 to 6 carbons;
R$_5$ and R$_5'$ independently are hydrogen, lower alkyl of 1 tp 6 carbons or halogen;
Y is S;
Z is n-alkyl having 2 to 10 carbons, cyclo or branchchained alkyl of 3 to 10 carbons, and straight chain alkenyl having 2 to 10 carbons, or cyclo or branched chained alkenyl of 3 to 10 carbons, and the Z-Y substituent is in a 1,2 (ortho) or 1,3 (meta) position on the phenyl ring relative to the ethene moiety;
A is (CH$_2$)$_n$ where n is 0–5, lower branched chain alkyl having 3 to 6 carbons, cycloalkyl having 3 to 6 carbons, alkenyl having 2 to 6 carbons and 1 to 2 double bonds, alkynyl having 2 to 6 carbons and 1 or 2 triple bonds;
B is COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5 to 10 carbons, or phenyl or lower alkylphenyl, R$_{11}$ is alkyl of 1 to 10 carbons, phenyl or lower alkylphenyl, R$_{12}$ is lower alkyl, and R$_{13}$ is divalent alkyl radical of 2–5 carbons.

11. A compound of claim 1 wherein Y is O.

12. A compound of the formula

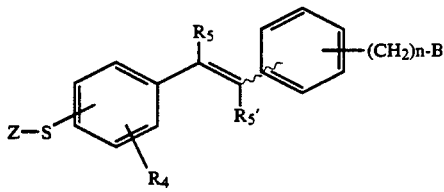

wherein $R_4$ is hydrogen or lower alkyl;

$R_5$ and $R_5'$ independently are hydrogen or lower alkyl;

Z is n-alkyl having 1 to 10 carbons, cyclo or branch-chained alkyl of 3 to 10 carbons, and straight chain alkenyl having 2 to 10 carbons, or cyclo or branched chained alkenyl of 3 to 10 carbons and the Z-S substituent is in a 1,2 (ortho) or 1,3 (meta) position on the phenyl ring relative to the ethene moiety;

n is is an integer between 0 to 5, and

B is H, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons phenyl or lower alkylphenyl, $R_{12}$ is lower alkyl, and $R_{13}$ is divalent alkyl radical of 2–5 carbons.

13. A compound of claim 12 where n is 0.

14. A compound of claim 12 wherein $R_4$ is in the 2'(ortho') position of the phenyl ring.

15. A compound of the formula

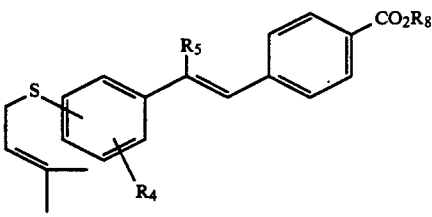

wherein $R_4$ is hydrogen or lower alkyl;

$R_5$ is hydrogen or lower alkyl, and $R_8$ is hydrogen or lower alkyl, and where the 3-methyl-2-thiobuten-1-yl substituent is in the 2 or in the 3 position of the phenyl ring.

16. A compound of claim 15 wherein $R_4$ is hydrogen.

17. A compound of claim 16 wherein the phenyl ring is 1,3 substituted.

18. A compound of claim 17 wherein $R_5$ is hydrogen.

19. The compound of claim 18 wherein $R_8$ is ethyl.

20. The compound of claim 18 wherein $R_8$ is hydrogen.

21. A compound of claim 17 wherein $R_5$ is $CH_3$.

22. The compound of claim 21 wherein $R_8$ is ethyl.

23. The compound of claim 21 wherein $R_8$ is hydrogen.

* * * * *

UNITED STATES PATENT AND TRADEMARK OFFICE
CERTIFICATE OF CORRECTION

PATENT NO. : 5,326,898
DATED : July 5, 1994
INVENTOR(S) : Roshantha A.S. Chandraratna It is certified that error appears in the above-identified patent and that said Letters Patent is hereby corrected as shown below:

Column 2, line 38, between "$R_3$" and "$R_4$" please add --and--;

Column 11, line 68, after "10" add --.--;

Column 12, line 36, "Formula 2" should be --Formula 1--;

Column 12, line 40, "Formula 2" should be --Formula 1--;

Column 13, line 65, "15" should be --1.5--;

Column 16, line 2, "S" should be --3--.

Column 17, line 53, "$Ch_2$" should be --$CH_2$--;

Column 18, line 49, "1 to 2" should be --1 or 2--.

Signed and Sealed this

Sixteenth Day of May, 1995

BRUCE LEHMAN

*Attest:*

*Attesting Officer*  *Commissioner of Patents and Trademarks*

UNITED STATES PATENT AND TRADEMARK OFFICE
CERTIFICATE OF CORRECTION

PATENT NO. : 5,326,898
DATED : July 5, 1994
INVENTOR(S) : Roshantha A.S. Chandraratna It is certified that error appears in the above-identified patent and that said Letters Patent is hereby corrected as shown below:

Column 3, line 55, after "reactions" delete ")";
Column 15, line 32-33, after "oil" delete "," and then before "BP" add --(--.

Signed and Sealed this

Thirteenth Day of June, 1995

Attest:

BRUCE LEHMAN

Attesting Officer

Commissioner of Patents and Trademarks